US012092602B2

(12) United States Patent
Westerhoff et al.

(10) Patent No.: US 12,092,602 B2
(45) Date of Patent: Sep. 17, 2024

(54) NANO-SIZED BORON-DOPED DIAMOND (BDD) ENABLED ELECTRODES

(71) Applicants: Paul K. Westerhoff, Scottsdale, AZ (US); Sergio Garcia-Segura, Tempe, AZ (US); Shahnawaz Sinha, Chandler, AZ (US); Rishabh Bansal, Tempe, AZ (US); Rafael Verduzco, Houston, TX (US); Michael S. Wong, Houston, TX (US)

(72) Inventors: Paul K. Westerhoff, Scottsdale, AZ (US); Sergio Garcia-Segura, Tempe, AZ (US); Shahnawaz Sinha, Chandler, AZ (US); Rishabh Bansal, Tempe, AZ (US); Rafael Verduzco, Houston, TX (US); Michael S. Wong, Houston, TX (US)

(73) Assignees: Arizona Board of Regents on behalf of Arizona State University, Scottsdale, AZ (US); William Marsh Rice University, Houston, TX (US)

( * ) Notice: Subject to any disclaimer, the term of this patent is extended or adjusted under 35 U.S.C. 154(b) by 248 days.

(21) Appl. No.: 17/206,935

(22) Filed: Mar. 19, 2021

(65) Prior Publication Data
US 2021/0293741 A1   Sep. 23, 2021

Related U.S. Application Data

(60) Provisional application No. 62/992,628, filed on Mar. 20, 2020.

(51) Int. Cl.
*G01N 27/30*   (2006.01)
*C02F 1/461*   (2023.01)

(52) U.S. Cl.
CPC ....... *G01N 27/308* (2013.01); *C02F 1/46109* (2013.01); *C02F 2001/46147* (2013.01)

(58) Field of Classification Search
CPC ............................ G01N 27/30–27/308; C02F 1/46109–2001/46147; C25B 11/043; C25B 11/083; C25B 11/055–11/071
See application file for complete search history.

(56) References Cited

U.S. PATENT DOCUMENTS

| | | | |
|---|---|---|---|
| 2004/0011643 A1* | 1/2004 | Davies | C12Q 1/001 422/98 |
| 2006/0144702 A1* | 7/2006 | Seki | C25B 11/073 427/249.1 |

OTHER PUBLICATIONS

Cunci et al ("Preparation and Electrochemistry of Boron-Doped Diamond Nanoparticles on Glassy Carbon Electrodes", Electrochemical and Solid-State Letters, 14 3, K17-K19, 2011). (Year: 2011).*

(Continued)

*Primary Examiner* — Alexander W Keeling
(74) *Attorney, Agent, or Firm* — Fish & Richardson P.C.

(57) ABSTRACT

An electrode includes an electrically conductive substrate with a coating containing boron-doped diamond (BDD) nanoparticles. Fabricating the electrode can include dispersing BDD nanoparticles in a solvent to yield a suspension, coating a conductive substrate with the suspension, and drying the suspension to yield the electrode. In some cases, fabricating the electrode includes combining BDD nanoparticles with a polymeric resin precursor to yield a mixture including a metal oxide, coating a conductive substrate with the mixture to yield a coated substrate, and calcining the coated substrate to yield a metal oxide coating including BDD nanoparticles. In certain cases, fabricating the electrode includes combining powdered activated carbon with polymeric linkers to yield a polymeric precursor solution, (Continued)

combining BDD nanoparticles with the polymeric precursor solution to yield a mixture, coating a conductive substrate with the mixture to yield a coated substrate, and crosslinking the polymeric linkers to yield the electrode.

9 Claims, 1 Drawing Sheet

(56) References Cited

OTHER PUBLICATIONS

Yang et al.("Diamond electrochemistry at the nanoscale: A review", Carbon, 2016, pp. 90-110). (Year: 2016).*
La-Torre-Riveros et al.("Diamond Nanoparticles as a Support for Pt and PtRu Catalysts for Direct Methanol Fuel Cells", ACS Appl. Mater. Interfaces, 2012, 4, 2, 1134-1147). (Year: 2012).*
Qi et al ("Enhanced selectivity of boron doped diamond electrodes for the detection of dopamine and ascorbic acid by increasing the film thickness", Applied Surface Science, vol. 390, Dec. 30, 2016, pp. 882-889). (Year: 2016).*
Lounasvuori et al ("Nanoparticle-Based Diamond Electrodes", Novel Aspects of Diamond, second edition, 2019, pp. 257-312). (Year: 2019).*
Einaga, "Development of electrochemical applications of boron-doped diamond electrodes," Bull. Chem. Soc. Jpn., 2018, 91:1752-1762.
Feng et al., "Electrochemical technologies for wastewater treatment and resource reclamation," Environ. Sci. Water Res. Technol., 2016, 2:800-831.
Garcia-Segura et al., "Electrochemical oxidation remediation of real wastewater effluents—a review," Process Safe Environ., 2018, 113:48-67.
Macpherson, "Practical Electrochemical Sensor using Boron Doped Diamond (BDD) Diamond Electrodes," Aug. 28, 2015, via Internet Archive: Wayback Machine URL: <https://web.archive.org/web/20201001145720/https://www.fierceelectronics.com/components/practical-electrochemical-sensors-using-boron-doped-diamond-bdd-diamond-electrodes>, retrieved on Mar. 30, 2022, URL<https://www.fierceelectronics.com/components/practical-electrochemical-sensors-using-boron-doped-diamond-bdd-diamond-electrodes>, 6 pages.
Montilla et al., "Synthetic Boron Doped Diamond Electrodes for Electrochemical Water Treatment," Bol. Grupo Español Carbon, Mar. 2014, 31:8-12.

* cited by examiner

NANO-SIZED BORON-DOPED DIAMOND (BDD) ENABLED ELECTRODES

CROSS-REFERENCE TO RELATED APPLICATION

This application claims the benefit of U.S. Patent Application No. 62/992,628 entitled "NANO-SIZED BORON-DOPED DIAMOND (BDD) ENABLED ELECTRODES" and filed on Mar. 20, 2020, which is incorporated by reference herein in its entirety.

STATEMENT OF GOVERNMENT INTEREST

This invention was made with government support under 1449500 awarded by The National Science Foundation. The government has certain rights in this invention.

TECHNICAL FIELD

This invention relates to fabrication of nano-sized boron-doped diamond enabled electrodes for water treatment and chemical sensing.

BACKGROUND

Electrochemical oxidation/reduction can be used to detect chemicals in aqueous solutions (e.g., water, bodily fluids, foods) and/or to treat pollutants in drinking and industrial wastewaters. For example, electrochemical oxidation can generate hydroxyl radicals (·OH), which are effective in degrading organic contaminants in water, or facilitate charge transfer of surface-bound electrons or hydrogen ($H_2$) to transform inorganic pollutants (e.g., nitrate). The electrochemical technology is based on utilizing electrons to mediate reactions, but being able to selectively utilize energy to oxidize (e.g., via ·OH) or reduce (e.g., electron transfer to nitrate) without energy going to competing reactions (e.g., oxygen or hydrogen evolution) can impact overall efficiency of water treatment processes. Electrochemical processes require at least two electrodes: an anode where oxidation occurs, and a cathode where reduction occurs. The system is powered with electrical energy to ensure the flow of electrodes during the electrolysis/electrocatalytic treatment. These electrodes are placed in a solution of enough conductivity (due to presence of electrolytes in solution) to close the electrochemical circuit.

Water splitting is another example of electrolysis in which water decomposes to oxygen gas at the anode, and hydrogen gas evolves at the cathode. However, this process requires external energy, around 1.23 V potential difference according to the standard reduction potentials, to split the water into gases. The range of electrode potential in which water is stable is referred to as its "electrochemical window." Certain materials require higher potentials than the standard reduction potential to oxidize water (oxygen evolution). The part that exceeds 1.23 V is called 'overpotential' or overvoltage to onset the reaction. It represents loss or nonideality in the electrochemical process, and results in the widening of the electrochemical window. The widening of the electrochemical window is a desired characteristic since it enables electrocatalytic processes of interest for water treatment, such as electrogeneration of reactive oxygen species (e.g., hydroxyl radical), enables a wide range of potentials for electroanalysis of target electroactive analytes with oxidation responses at potential higher than 1.23 V vs SHE, and diminishes competitive water oxidation reactions (increases faradaic efficiencies of other electrochemical reactions).

Non earth abundant or rare-earth elements (e.g. platinum (Pt), gold (Au)) and other metals (e.g., copper, nickel) are often used in electrode materials. However, these can be costly, have short operational lifetimes or release metals of health or regulator concern into water (e.g., copper, nickel). While many forms of carbon electrodes (e.g., graphite, graphene, carbon nanotubes) have been commercialized or patented because carbon is earth-abundant and inexpensive, these electrodes often suffer from poor electrochemical performance attributes and material durability.

SUMMARY

Boron-doped diamond (BDD) acts like a semiconductor and demonstrates conductance similar to that of metals. BDD includes earth-abundant elements (carbon, oxygen, boron). BDD has a high oxygen evolution overvoltage, and can degrade organic pollutants without impacting the electrode material. BDD has good corrosion stability even in acidic media and provides a wide electrochemical potential window −1.2V to +2.5V. This widening of the electrochemical window is advantageous for contaminant degradation, in which higher overpotential enhances further oxygen or hydrogen evolution and formation of hydroxyl radicals (·OH) or reactive electrons, respectively, which are effective for electrochemical degradation of various contaminants in water. However, current fabrication methods of BDD electrodes are expensive, typically require specialized equipment (e.g., chemical vapor deposition processes), and are limited to electrode substrates compatible with those specialized processes.

In a first general aspect, an electrode includes an electrically conductive substrate and a coating on the electrically conductive substrate. The coating includes boron-doped diamond nanoparticles.

Implementations of the first general aspect may include one or more of the following features.

The boron-doped diamond nanoparticles can have a diameter in a range between about 10 nm and about 200 nm, or in a range between about 50 nm and about 60 nm. The electrode can include between about 10 and about 20,000 μg boron-doped diamond/g substrate. The substrate can include one or more of silicon, titanium, carbon cloth, carbon felt, indium tin oxide, and an electrically conductive polymer. A thickness of the coating is typically in a range between 1 nanoparticle and 5 nanoparticles.

In a second general aspect, fabricating an electrode includes dispersing boron-doped diamond nanoparticles in a solvent to yield a suspension, coating an electrically conductive substrate with the suspension, and drying the suspension to yield the electrode.

Implementations of the second general aspect may include one or more of the follow features. The suspension can include a binder, such as an ionomer. The solvent can include an alcohol (e.g., one or more of methanol, ethanol, an isopropanol). Coating the substrate with the suspension can include dip coating, drop casting, spray coating, or spin coating.

In a third general aspect, fabricating an electrode includes combining boron-doped diamond nanoparticles with a polymeric resin precursor to yield a mixture including a metal oxide, coating an electrically conductive substrate with the mixture to yield a coated substrate, and calcining the coated substrate to yield a metal oxide coating including boron-doped diamond nanoparticles.

Implementations of the third general aspect may include one or more of the follow features.

The metal oxide can include metal oxide can include one or more of $RuO_2$, $TiO_2$, $IrO_2$, $SnO_2$, and $Sb$—$SnO_2$. The mixture can include a homogeneous suspension of boron-doped diamond nanoparticles and metal ion precursors dissolved in an ionic liquid. The ionic liquid can include one or both of methylimidizolium hydrogensulfate and pyridinium chloride. In some cases, the mixture includes an organic acid (e.g., one or more of citric acid, ascorbic acid, and formic acid) and ethylene glycol. In certain cases, the mixture includes an alcohol. When the mixture includes an alcohol, the mixture can be in the form of a sol-gel. When the mixture is in the form of a sol-gel, the mixture can further include an organic acid (e.g., one or more of acetic acid, formic acid, and citric acid). The third general aspect may further include heating the mixture to at least 90° C. before coating the substrate with the mixture. Coating the substrate can include dip coating, brush painting, or spray coating.

In a fourth general aspect, fabricating an electrode includes combining powdered activated carbon with polymeric linkers to yield a polymeric precursor solution, combining boron-doped diamond nanoparticles with the polymeric precursor solution to yield a mixture, coating an electrically conductive substrate with the mixture to yield a coated substrate, and crosslinking the polymeric linkers to yield the electrode.

Implementations of the fourth general aspect may include one or more of the following features.

The polymeric linker can include polyvinyl alcohol or glutaraldehyde. Crosslinking can include thermal curing, ultraviolet curing, or electrochemical polymerization.

Electrodes coated or embedded with nanoparticles of boron-doped diamond (nano-BDD) provide greater electroactive surface area than that of bulk BDD and can be integrated into polymeric, metallic, and graphitic electrodes of nearly any size or geometrical shape. This disclosure describes fabrication of electrodes using nano-BDD and applications of nano-BDD enabled electrodes for sensing and treatment of pollutants in aqueous solutions. Unique electrochemical properties occur when nano-BDD is used within the described electrodes, allow for >1000× higher BDD surface area per unit area of electrodes, and enable fabrication of electrodes at <1% of the cost compared to conventional BDD electrodes.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

Figures 1A, 1B:
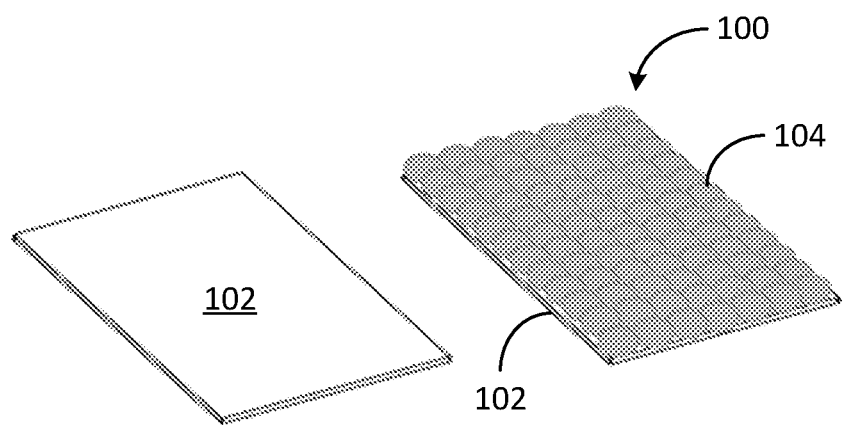
FIG. 1A an electrode with boron-doped diamond (BDD) nanoparticles.
FIG. 1B depicts the electrically conductive substrate in FIG. 1A.

This disclosure describes the design, fabrication, and use of electrodes coated or embedded with nanoparticles of boron-doped diamond ("nano-BDD electrodes"). FIG. 1A depicts electrode 100 with electrically conductive substrate 102 and boron-doped diamond nanoparticles 104. FIG. 1B depicts electrically conductive substrate 102. Although electrically conductive substrate 102 is depicted as a planar rectangle, the substrate can be of any size or shape. Electrode 100 is suitable for use in applications such as chemical sensing, water splitting, and pollutant remediation, or other applications. The BDD nanoparticles are typically about 10 nm to about 200 nm (e.g., about 50 nm to about 60 nm) in diameter. The surface area of the nano-BDD electrodes typically exceeds that of BDD electrodes formed with macrocrystalline BDD by several orders of magnitude.

Nano-BDD electrodes are fabricated using commercially available nano-BDD particles of size below 1000 nm with boron doping levels up to about 20,000 μg BDD/g electrode material (e.g., from about 10 to about 20,000 μg BDD/g electrode material). Commercially available diamond electrode nanoparticles can be produced using different dopants, including but not limited to boron, nitrogen, phosphorus, or any combination thereof. Nano-BDD can be surface functionalized and dispersed in liquids or solids. Suitable electrode substrates include conductive and semi-conductive substrates, such as silicon, titanium, carbon cloth, carbon felt, indium tin oxide, and conductive polymers.

In a first implementation, nano-BDD particles are dispersed in a solution containing volatile solvent (e.g., an alcohol such as isopropanol, ethanol, methanol) to yield a nano-BDD suspension. The nano-BDD suspension may also contain a binder (e.g., an ionomer such as Nafion®). The nano-BDD suspension is sonicated to ensure homogeneous distribution of the BDD nanoparticles, thereby yielding a "nano-BDD ink." A substrate is coated with the nano BDD-ink by a method such as dip-coating, drop-casting, spray-coating, or spin-coating. The coating is dried at a temperature in a range between ambient temperature and 300° C. The procedure facilitates the evaporation of the volatile solvent and the adhesion of the BDD nanoparticles to the substrate surface to yield the nano-BDD electrode.

In another implementation, nano-BDD particles are mixed with a polymeric resin precursor and one or more metal precursors (e.g., $RuCl_3$, $SbCl_3$, $IrCl_3$) to form metal oxide or mixed metal oxide layers including, for example, $RuO_2$, $TiO_2$, $IrO_2$, $SnO_2$, $Sb$—$SnO_2$, or a combination thereof. Layers of nano-BDD/metal oxide coatings are then deposited on a substrate in a method such as an ionic-liquid method, the Pechini method, or a sol-gel method. The ionic liquid method includes homogeneous suspension of nano-BDD in an ionic liquid solution (e.g., including methylimidazolium hydrogensulfate or pyridinium chloride) including metal oxide precursors (e.g., $RuCl_3$, $SbCl_3$, $IrCl_3$). The Pechini method includes combining nano-BDD particles and metal oxide precursors in organic acid (e.g., citric acid or ascorbic acid) and ethylene glycol under different molar ratios to yield a mixture. The mixture is heated up to 90° C. prior to deposition. The sol-gel method includes the preparation of sol-gel solutions containing nano-BDD particles in an alcohol with an organometallic precursor (e.g., ruthenium (III) acetylacetonate, iridium acetylacetonate, etc). Suitable alcohols include isopropanol, ethanol, and methanol. The addition of an organic acid such as acetic acid, formic acid, or citric acid promotes the formation of a sol-gel. The sol-gel solutions are deposited on a selected substrate by a procedure such as dip-coating, brush-painting, or spin-coating. The deposited solution is calcined to eliminate organic materials and to form metallic oxide coatings with nano-BDD that remains on the coating surface or is embedded within the coating.

In another implementation, conductive polymeric electrodes with nano-BDD particles are prepared following in situ polymeric processes. Powdered activated carbon (PAC) is mixed with a polymeric linker such as polyvinyl alcohol and glutaraldehyde using water or other solvent. Nano-BDD particles can then be mixed and homogenized with the polymeric precursor solution or distributed on the polymeric surface before crosslinking. Electrode dimensions, porosity, and thickness can be controlled by, for example, a flow-coating method prior to conducting crosslinking under vacuum oven conditions at temperatures ranging between about 30° C. and about 300° C. Other crosslinking methods can also be applied, such as UV curing. Direct electrochemical polymerization methods to embed BDD-nanoparticles can also be conducted to manufacture nano-BDD electrodes, including polymers such as polypyrrole, polyaniline, polyphenylene vinylene, or a combination thereof.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. An electrode comprising:
   an electrically conductive substrate; and
   a coating on the electrically conductive substrate, wherein the coating comprises a polymer, powdered activated carbon, and boron-doped diamond nanoparticles comprising between about 10 and about 80,000 ppm boron.
2. The electrode of claim 1, wherein the boron-doped diamond nanoparticles have a diameter in a range between about 10 nm and about 200 nm.
3. The electrode of claim 2, wherein the boron-doped diamond nanoparticles have a diameter in a range between about 50 nm and about 60 nm.
4. The electrode of claim 1, wherein a thickness of the coating is in a range between one nanoparticle and five nanoparticles.
5. The electrode of claim 1, wherein the polymer further comprises polypyrrole.
6. The electrode of claim 1, wherein the polymer comprises polyaniline.
7. The electrode of claim 1, wherein the polymer comprises polyphenylene vinylene.
8. The electrode of claim 1, wherein the polymer comprises polyvinyl alcohol.
9. The electrode of claim 8, wherein the polymer further comprises glutaraldehyde linkers.

* * * * *